US006119690A

United States Patent [19]

Pantaleo

[11] Patent Number: 6,119,690

[45] Date of Patent: Sep. 19, 2000

[54] NOSTRIL FILTER SYSTEM

[76] Inventor: Joseph M. Pantaleo, 1403 W. 12th Ave., Melrose Park, Ill. 60160

[21] Appl. No.: 09/206,091

[22] Filed: Dec. 4, 1998

[51] Int. Cl.[7] .................... A61M 16/00

[52] U.S. Cl. .................... 128/206.11; 128/863

[58] Field of Search .................... 128/206.11, 206.18, 128/207.18, 207.12, 207.13, 205.24, 863, 203.22

[56] References Cited

U.S. PATENT DOCUMENTS

| | | | |
|---|---|---|---|
| 2,277,390 | 3/1942 | Crespo | 128/148 |
| 3,905,335 | 9/1975 | Kapp | 128/140 N |
| 4,052,983 | 10/1977 | Bovender | 128/140 N |
| 4,267,831 | 5/1981 | Aguilar | 128/203.14 |
| 5,417,205 | 5/1995 | Wang | 128/206.11 |
| 5,425,359 | 6/1995 | Liou | 128/206.11 |
| 5,485,836 | 1/1996 | Lincoln | 128/206.11 |
| 5,568,808 | 10/1996 | Rimkus | 128/206.11 |
| 5,890,491 | 4/1999 | Rimkus | 128/206.11 |

FOREIGN PATENT DOCUMENTS

| | | | |
|---|---|---|---|
| 2610830 | 2/1987 | France | 128/207.18 |
| 85/01216 | 3/1985 | WIPO | 128/206.11 |

*Primary Examiner*—Aaron J. Lewis
*Assistant Examiner*—Teena Mitchell
*Attorney, Agent, or Firm*—Joseph N. Breaux

[57] ABSTRACT

A nostril filter system that includes a filter assembly including a foam rubber nose insert member including a tubular nasal passage portion and a dome shaped naris portion; a pliable plastic insert member including a tubular top portion and a dome shaped bottom portion; a cone-shaped, second stage filter element; and a disk-shaped, first stage filter element; the second and first stage filter elements being insertable into the pliable plastic insert member in that order prior to inserting the pliable plastic insert member into the foam rubber nose insert member; the foam rubber nose insert member being insertable into a nostril of a user such that the tubular nasal passage portion is inserted into the opening of the user's nasal passage and the dome shaped naris portion is positioned within the naris chamber of the user's nostril. The system can also include a nose shroud member and two identical nose insert member holding structures that are detachably connectable to the nose shroud member.

3 Claims, 3 Drawing Sheets

FIG5A
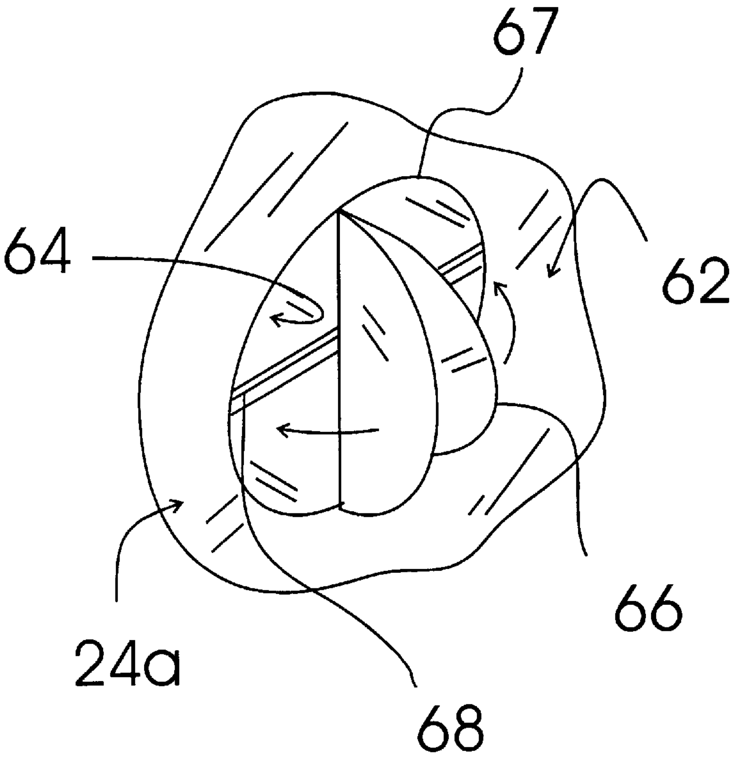
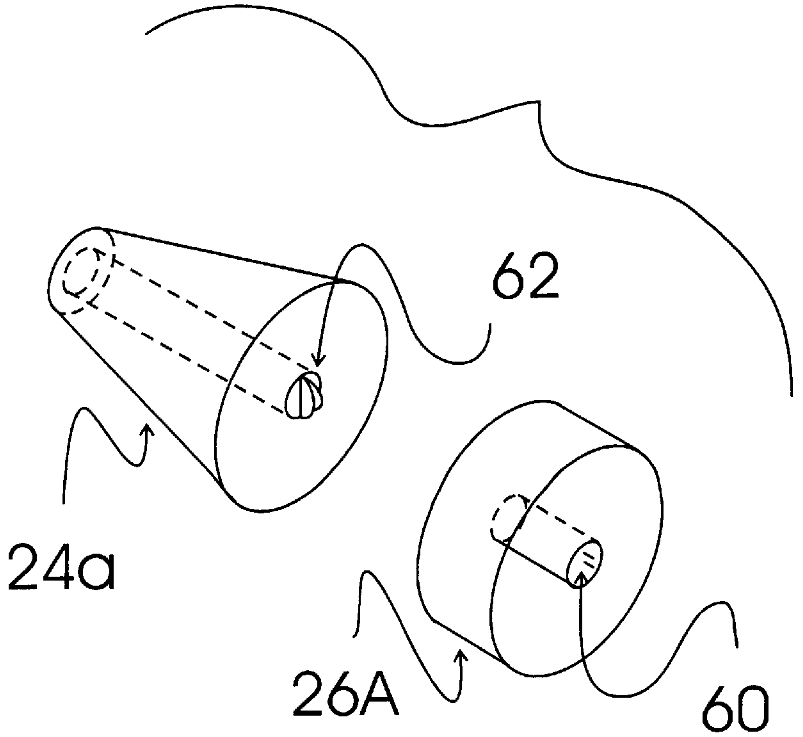
FIG5

NOSTRIL FILTER SYSTEM

TECHNICAL FIELD

The present invention relates to breathing filters and more particularly to nasal filter system including a filter assembly including a foam rubber nose insert member including a tubular nasal passage portion and a dome shaped naris portion; a pliable plastic insert member including a tubular top portion and a dome shaped bottom portion; a cone-shaped, second stage filter element; and a disk-shaped, first stage filter element; the second and first stage filter elements being insertable into the pliable plastic insert member in that order prior to inserting the pliable plastic insert member into the foam rubber nose insert member; the foam rubber nose insert member being insertable into a nostril of a user such that the tubular nasal passage portion is inserted into the opening of the user's nasal passage and the dome shaped naris portion is positioned within the naris chamber of the user's nostril.

BACKGROUND ART

Many individuals suffer from allergies triggered by air borne allergens. It would be a benefit to these individuals to have a filter system that could be used to filter out the allergens prior to reaching the nasal passageways. In addition, because there are many social situations where an individual would not wish to call attention to himself by wearing a face mask, it would be a further benefit to have a filter system that included a filter assembly that could be positioned within the nostril of a wearer. It would be a further benefit to have such a filter system with a nostril insertable filter assembly that also included a nose shroud for covering the nose of the wearer and providing additional filtering elements for prefiltering the air prior to reaching the nostril insertable filter assembly for those individuals in a situation where such a cover device would not pose a problem.

GENERAL SUMMARY DISCUSSION OF INVENTION

It is thus an object of the invention to provide a nostril filter system that includes a filter assembly that is insertable into the nostril of user.

It is a further object of the invention to provide a nostril filter system that includes to filter assemblies and a nose covering shroud having a filter panel for prefiltering the air before reaching the filter assembly.

It is a still further object of the invention to provide a nostril filter system that includes a filter assembly including a foam rubber nose insert member including a tubular nasal passage portion and a dome shaped naris portion; a pliable plastic insert member including a tubular top portion and a dome shaped bottom portion; a cone-shaped, second stage filter element; and a disk-shaped, first stage filter element; the second and first stage filter elements being insertable into the pliable plastic insert member in that order prior to inserting the pliable plastic insert member into the foam rubber nose insert member; the foam rubber nose insert member being insertable into a nostril of a user such that the tubular nasal passage portion is inserted into the opening of the user's nasal passage and the dome shaped naris portion is positioned within the naris chamber of the user's nostril.

It is a still further object of the invention to provide a nostril filter system that accomplishes some or all of the above objects in combination.

Accordingly, a nostril filter system is provided. The nostril filter system includes a filter assembly including a foam rubber nose insert member including a tubular nasal passage portion and a dome shaped naris portion; a pliable plastic insert member including a tubular top portion and a dome shaped bottom portion; a cone-shaped, second stage filter element; and a disk-shaped, first stage filter element; the second and first stage filter elements being insertable into the pliable plastic insert member in that order prior to inserting the pliable plastic insert member into the foam rubber nose insert member; the foam rubber nose insert member being insertable into a nostril of a user such that the tubular nasal passage portion is inserted into the opening of the user's nasal passage and the dome shaped naris portion is positioned within the naris chamber of the user's nostril.

In a preferred embodiment the nostril filter system includes two of the nostril filter assemblies described herein above plus a nose shroud member and two identical nose insert member holding structures that are detachably connectable to the nose shroud member; the nose shroud member including a nose receiving compartment defined by an outer shroud shell having two HEPA filtering panels and a bottom surface having two sets of insert member holding attachment openings; each nose insert member holding structure holding one of the filter assemblies therein with an air intake opening provided between a bottom surface of the shroud member and a bottom edge of the nose insert member holding structure. Each nose insert member holding structures includes a number of stand off members each terminating in a fastener tip that detachably fastens to the bottom surface of the shroud member within the one of the sets of insert member holding attachment openings.

BRIEF DESCRIPTION OF DRAWINGS

For a further understanding of the nature and objects of the present invention, reference should be had to the following detailed description, taken in conjunction with the accompanying drawings, in which like elements are given the same or analogous reference numbers and wherein.

1 therein with an air intake opening provided between the bottom surface of the shroud member and the bottom edge of the nose insert member holding structure.

Figure 3:
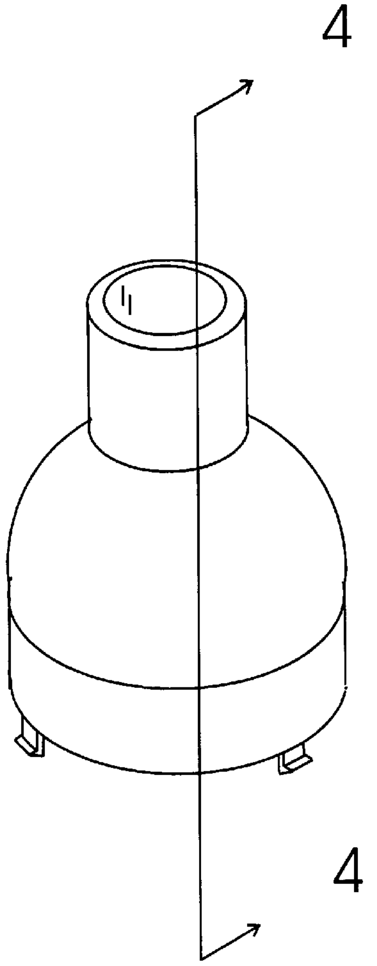

FIG. 3 is perspective view of one of the two identical nose insert member holding structures showing two of the three identical stand off members each terminating in a fastener tip that detachably fastens to the bottom surface of the shroud member within the insert member holding attachment openings.

Figure 1:
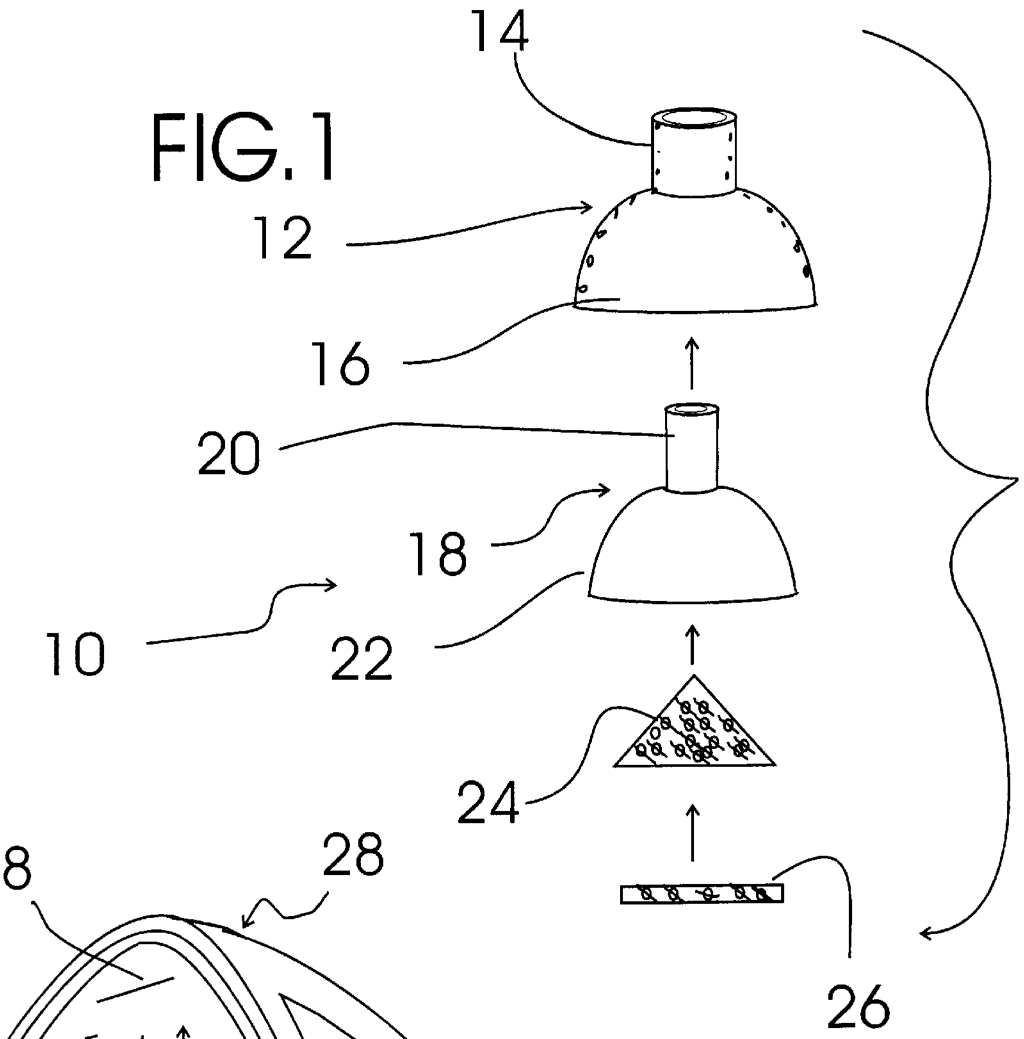
FIG. 1 is a perspective view of a first exemplary embodiment of a filter assembly of the nasal filter system of the present invention showing the foam rubber nose insert member including the tubular nasal passage portion and the dome shaped naris portion; the pliable plastic insert member including the tubular top portion and the dome shaped bottom portion; the cone-shaped, second stage filter element; and the disk-shaped, first stage filter element; the second and first stage filter elements being inserted into the pliable plastic insert member in that order prior to inserting the pliable plastic insert member into the foam rubber nose insert member; the foam rubber nose insert member being insertable into the nostril of a user with the tubular nasal passage portion inserted into the opening of the user's nasal passage and the dome shaped naris portion positioned within the naris chamber of the user's nostril.
Figure 4:
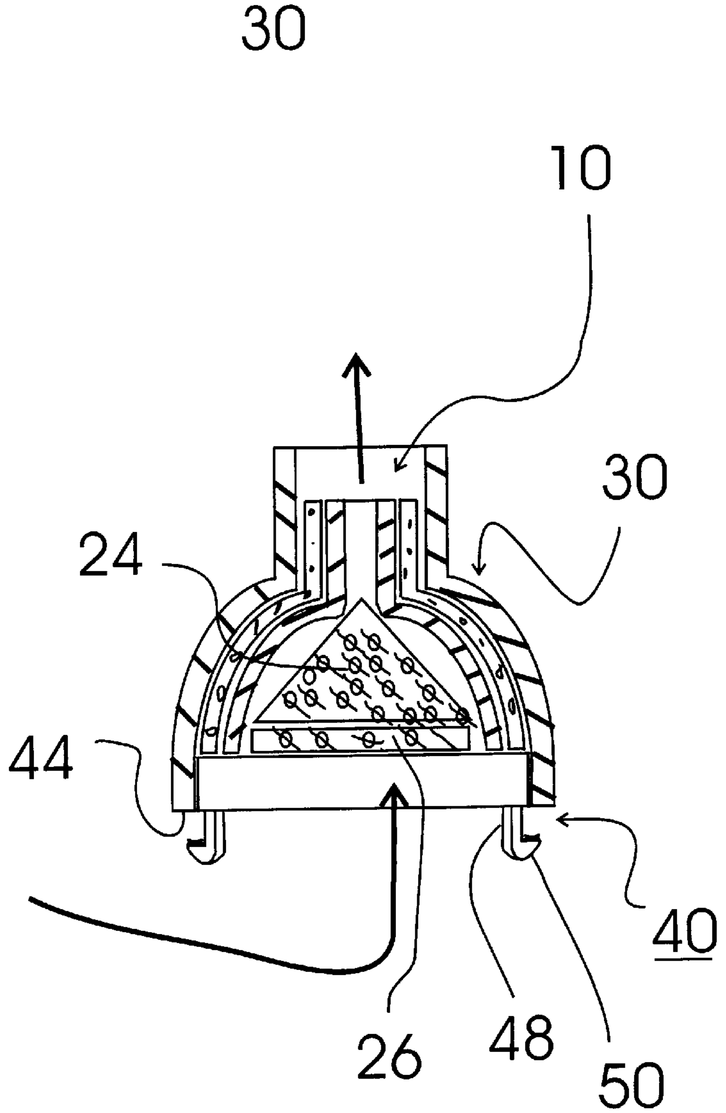

FIG. 4 is a sectional view of the nose insert holding structure of FIG. 3 with the filter assembly of FIG. 1 installed therein showing the second and first stage filter elements inserted into the pliable plastic insert member, the pliable plastic insert member inserted into the foam rubber nose insert member, and the foam rubber insert member inserted into the nose insert holding structure such that air flowing through the nose insert holding structure must pass through the first and second stage filter elements.

FIG. 5 is a second exemplary embodiment of a cone-shaped second stage filter element.

FIG. 5A is the one-way air outlet valve of the embodiment of FIG. 5.

EXEMPLARY MODE FOR CARRYING OUT THE INVENTION

FIG. 1 shows an exemplary filter assembly, generally designated 10, of the nasal filter system of the present invention. Filter assembly 10 includes a hollow, foam rubber nose insert member, generally designated 12, including a tubular nasal passage portion 14 and a dome shaped naris portion 16; a hollow, pliable plastic insert member, generally designated 18, including a tubular top portion 20 and a dome shaped bottom portion 22; a cone-shaped, second stage filter element 24; and a disk-shaped, first stage filter element 26. Second stage filter element 24 and first stage filter element 26 are HEPA filters. During assembly, second and first stage filter elements 24,26 are inserted into pliable plastic insert member 18 in that order prior to inserting pliable plastic insert member 18 into foam rubber nose insert member 12. Foam rubber nose insert member 12 is insertable into the nostril of a user with tubular nasal passage portion 14 inserted into the opening of the user's nasal passage and dome shaped naris portion 16 positioned within the naris chamber of the user's nostril.

Figure 2:
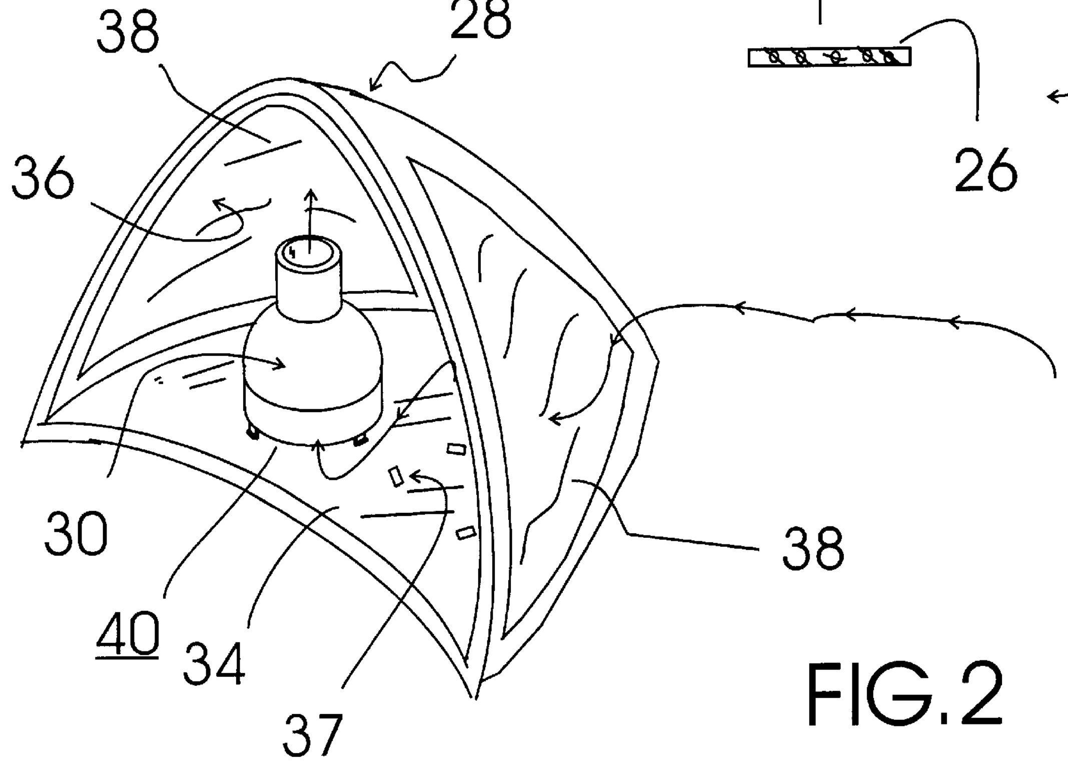
FIG. 2 is a perspective view of a second exemplary embodiment of the nostril filter system of the present invention that includes two of the nostril filter assemblies of FIG. 1 plus a nose shroud member and two identical nose insert member holding structures (only one shown) that are detachably connectable to the nose shroud member; the nose shroud member including a nose receiving compartment defined by an outer shroud shell having two HEPA filtering panels and a bottom surface having two sets of insert member holding attachment openings; each nose insert member holding structure holding a filter assembly of FIG.

FIG. 2 shows a nose shroud member, generally designated 28, that is provided in a second exemplary nostril filter system along with two identical nose insert member holding structures, generally designated 30, (only one shown). Nose insert member holding structures 30 are detachably connectable to a bottom surface 34 of nose shroud member 28. Bottom surface 34 includes two sets of insert member holding attachment openings 37 (only one shown) and partially defines a nose receiving compartment 36 within which the user positions his/her nose with a nose insert holding structure 30 installed in each nostril. Nose shroud member 28 includes two HEPA filtering panels 38 that prefilter the air entering nose receiving compartment 36. Referring to FIG. 3, each nose insert member holding structure 30 is adapted, with reference to FIG. 4, to hold a filter assembly 10 and form an air intake opening 40 (see also FIG. 2) between a bottom surface 34 (FIG. 2) of shroud member 28 and a bottom edge 44 of nose insert member holding structure 30. Each nose insert member holding structure 30 includes three standoffs 48 that terminate with a fastener tip 50 that are snap fittable into a set of insert member holding attachment openings 37 (FIG. 2). In use, first stage filtering element 26 can be replaced with greater frequency than second stage filtering element 24 if desired.

FIG. 5 shows a second exemplary embodiment of a cone-shaped, second stage filter element, generally designated 24*a* and a second exemplary embodiment of a disk-shaped, first stage filter element, generally designated 26*a*. Disk-shaped, first stage filter element 26*a* is identical to disk-shaped, first stage filter element 26 (FIG. 1) except a cylinder shaped outlet air passageway 26 is formed through the center thereof. Cone-shaped, second stage filter element 24*a* is identical to cone-shaped, second stage filter element 24 (FIG. 1) except that cone-shaped, second stage filter element 24*a* has a one-way air outlet valve, generally designated 62 provided through the center thereof. Referring to FIG. 5A, one-way air outlet valve 62 includes an air passageway 64 having a flexible circular flap 66 attached across the center of outlet opening 67 thereof and a flap stop 68 oriented across outlet opening 67 in a manner to allow circular flap 66 to prevent air from entering through outlet opening 67 when the user is inhaling but allowing the free passage of air out through outlet opening 67 when the user is exhaling.

It can be seen from the preceding description that a nostril filter system has been provided that includes a filter assembly including a foam rubber nose insert member including a tubular nasal passage portion and a dome shaped naris portion; a pliable plastic insert member including a tubular top portion and a dome shaped bottom portion; a cone-shaped, second stage filter element; and a disk-shaped, first stage filter element; the second and first stage filter elements being insertable into the pliable plastic insert member in that order prior to inserting the pliable plastic insert member into the foam rubber nose insert member; the foam rubber nose insert member being insertable into a nostril of a user such that the tubular nasal passage portion is inserted into the opening of the user's nasal passage and the dome shaped naris portion is positioned within the naris chamber of the user's nostril; and that includes two of the nostril filter assemblies described herein above plus a nose shroud member and two identical nose insert member holding structures that are detachably connectable to the nose shroud member; the nose shroud member including a nose receiving compartment defined by an outer shroud shell having two HEPA filtering panels and a bottom surface having two sets of insert member holding attachment openings; each nose insert member holding structure holding one of the filter assemblies therein with an air intake opening provided between a bottom surface of the shroud member and a bottom edge of the nose insert member holding structure. Each nose insert member holding structures includes a number of stand off members each terminating in a fastener tip that detachably fastens to the bottom surface of the shroud member within the one of the sets of insert member holding attachment openings.

It is noted that the embodiment of the nostril filter system described herein in detail for exemplary purposes is of course subject to many different variations in structure, design, application and methodology. Because many varying and different embodiments may be made within the scope of the inventive concept(s) herein taught, and because many modifications may be made in the embodiment herein detailed in accordance with the descriptive requirements of the law, it is to be understood that the details herein are to be interpreted as illustrative and not in a limiting sense.

What is claimed is:

1. A nostril filter system comprising:

a first filter assembly including:

a foam rubber nose insert member including a tubular nasal passage portion and a dome shaped naris portion;

a pliable plastic insert member including a tubular top portion and a dome shaped bottom portion;

a cone-shaped, second stage filter element; and a disk-shaped, first stage filter element;

said second and first stage filter elements being insertable into said pliable plastic insert member in that order prior to inserting said pliable plastic insert member into said foam rubber nose insert member;

said foam rubber nose insert member being insertable into a nostril of a user such that said tubular nasal passage portion is insertable into an opening of a user's nasal passage and said dome shaped naris portion is positioned within a naris chamber of a user's nostril.

2. The nostril filter system of claim 1 further including:

a second filter assembly identical to said first filter assembly;

a nose shroud member; and two identical nose insert member holding structures that are detachably connectable to said nose shroud member;

said nose shroud member including a nose receiving compartment defined by an outer shroud shell having two filtering panels and a bottom surface having two sets of insert member holding attachment openings;

each said identical nose insert member holding structure holding one of said first and said second filter assemblies therein with an air intake opening provided between a bottom surface of said shroud member and a bottom edge of said nose insert member holding structure;

each said nose insert member holding structures including a number of stand off members each terminating in a fastener tip that detachably fastens to said bottom surface of said shroud member within said one of said sets of insert member holding attachment openings.

3. The nostril filter system of claim 1 wherein:

said cone-shaped, second stage filter element includes a cylinder shaped outlet air passageway formed through a center thereof; and said cone-shaped, second stage filter element includes a one-way air outlet valve provided through a center thereof.

* * * * *